(12) United States Patent
Keshishian

(10) Patent No.: US 8,979,260 B1
(45) Date of Patent: Mar. 17, 2015

(54) CONTACT LENSES WITH INDICATORS

(71) Applicant: Indicator Systems International, Inc., Newport Beach, CA (US)

(72) Inventor: Craig Keshishian, Newport Beach, CA (US)

(73) Assignee: Indicator Systems International, Inc., Newport Beach, CA (US)

( * ) Notice: Subject to any disclaimer, the term of this patent is extended or adjusted under 35 U.S.C. 154(b) by 29 days.

(21) Appl. No.: 13/651,222

(22) Filed: Oct. 12, 2012

Related U.S. Application Data

(60) Provisional application No. 61/548,649, filed on Oct. 18, 2011.

(51) Int. Cl.
*G02C 7/04* (2006.01)

(52) U.S. Cl.
CPC ..................................... *G02C 7/049* (2013.01)
USPC ............. 351/159.02; 351/159.04; 351/159.24

(58) Field of Classification Search
CPC ....... A61L 12/00; A61L 12/08; A61L 12/082; G02C 7/04; A61K 2201/00; A61K 2201/01; A61K 2201/012
USPC ............. 351/159.04–159.06, 159.28, 159.69, 351/159.8
See application file for complete search history.

(56) References Cited

U.S. PATENT DOCUMENTS

| | | | |
|---|---|---|---|
| 5,158,718 A | 10/1992 | Thakrar et al. | |
| 5,443,987 A * | 8/1995 | DeCicco et al. | 435/4 |
| 6,258,591 B1 * | 7/2001 | Yoneda et al. | 435/264 |
| 7,041,063 B2 * | 5/2006 | Abreu | 600/549 |
| 7,560,421 B2 * | 7/2009 | Nakada et al. | 510/112 |
| 8,518,374 B2 * | 8/2013 | Boga et al. | 424/10.3 |
| 8,524,861 B2 * | 9/2013 | Dobson et al. | 530/326 |
| 2006/0222675 A1 * | 10/2006 | Sabnis et al. | 424/405 |
| 2007/0016074 A1 * | 1/2007 | Abreu | 600/475 |
| 2008/0012164 A1 | 1/2008 | Phelan et al. | |
| 2008/0181931 A1 * | 7/2008 | Qiu et al. | 424/429 |
| 2009/0303440 A1 * | 12/2009 | Heacock et al. | 351/219 |
| 2010/0317745 A1 | 12/2010 | Nicolson et al. | |
| 2011/0170055 A1 * | 7/2011 | Enerson | 351/160 R |
| 2011/0230588 A1 | 9/2011 | Devlin et al. | |
| 2011/0287464 A1 * | 11/2011 | Restaino | 435/18 |

* cited by examiner

*Primary Examiner* — Suchin Parihar
*Assistant Examiner* — William R Alexander
(74) *Attorney, Agent, or Firm* — Foley & Lardner LLP

(57) ABSTRACT

This invention relates to contact lenses comprising pH indicating moieties useful for determining the presence or absence of active bacterial infections wherein said pH indicator is entrapped in the lens. Other aspects relate to contact lenses comprising pH indicating moieties useful for determining the presence or absence of active bacterial infections and a biodegradable coating with a biocompatible colorant entrapped within the coating useful for determining the usable lifespan of the contact lens. Other aspects relate to methods of using such contact lenses.

11 Claims, 1 Drawing Sheet

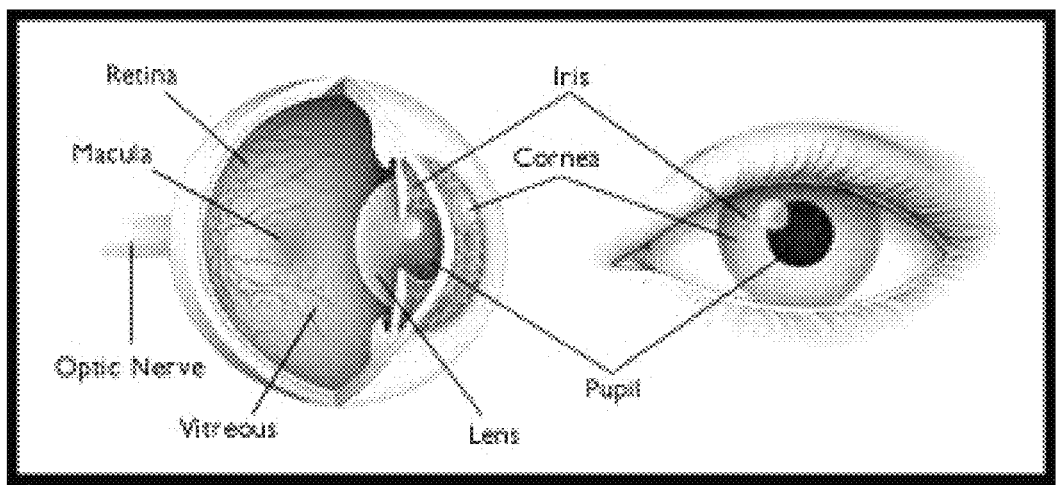

CONTACT LENSES WITH INDICATORS

CROSS-REFERENCE TO RELATED APPLICATIONS

This application claims the benefit under 35 U.S.C. §119 (e) of U.S. Provisional Ser. No. 61/548,649, filed on Oct. 18, 2011, which is incorporated herein by reference in its entirety.

BACKGROUND OF THE INVENTION

1. Field of the Invention

This invention is directed to hydrogel contact lenses having one or more indicators contained therein.

2. State of the Art

Individuals who wear contact lenses run an increased risk of serious eye infections. See, for example, www.ophthobook.com/chapters/infections. Often, the onset of the infection is difficult to discern until the infection becomes quite serious. The problem is complicated by virtue of the fact that many contact lens wearers are not compliant with proper maintenance of their lenses and the recommended time for replacing the lenses. Either or both of these factors increase the likelihood of infection.

Accordingly, there is an ongoing need to provide the contact lens wearer with an indication of a bacterial eye infection as quickly as possible and well before the infection becomes serious. There is also a need for contact lens markers which would allow the wearer to know when the lens is no longer suitable for use.

SUMMARY OF THE INVENTION

This invention is directed to hydrogel contact lenses (soft lenses) having one or more indicators entrapped in the lens. In one embodiment, the indicator is a pH indicator and preferably is a pH indicator which is optically transparent at the pH of normal eye fluids which is about 7.4. However, in the presence of a growing bacterial population, the indicator will become colored indicating to the wearer the presence of an eye infection.

In another embodiment of this invention, there is provided a contact lens having a pH indicator in at least a portion thereof which indicator is optically clear at a pH of from about 6.8 to 7.6 and which becomes colored at a pH of less than about 6.5. Preferably, the indicator is contained only in the area outside of the pupil portion of the contact lens such that vision of the wearer is minimally impaired by the color change.

The pH indicator is preferably entrapped within the contact lens so that there is little to no leaching of the indicator from the lens. In one embodiment, the contact lens is mildly crosslinked so to further entrap the pH indicator therein.

When a bacterial infection is initiated in the eye, there is a corresponding release of bacterial byproducts such as $CO_2$, hydrogen sulfide, sulfur dioxide, ammonium, lactate, and mixtures thereof result in the eye fluid becoming more acidic. Typically, the pH under the lens can drop to as low as about 5.2 due to the accumulation of such byproducts. At that pH, the pH indicator will become colored or change colors. Preferred indicators include, by way of example only, hexamethoxy red and heptamethoxy red.

In yet another embodiment of this invention, there is provide a hydrogel contact lens which indicates to the wearer that the lens is no longer suitable for use. In this embodiment, there is provided a contact lens comprising particles which contain a biodegradable outer layer and the interior comprises a colorant. Biodegradation of the exterior of the particles is predicated by use of an eye enzyme or other factor in the exterior of the particles and degradation time is selected such that release of the colorant indicates that the lens is no longer suitable for use.

In a method aspect, this invention provides for a method for assessing whether the eye of the wearer has an active bacterial infection which method comprises detecting the presence or absence of a colorimetric change in the pH indicator entrapped within the lens in the manner described above; correlating the presence or absence of a colorimetric change in the pH indicator with the presence of an active bacterial infection on the lens; and wherein a colorimetric change correlates to the presence of an active bacterial infection and the lack of a colorimetric change correlates to the absence of an active bacterial infection.

BRIEF DESCRIPTION OF THE DRAWINGS

FIG. 1 depicts a diagram of the eye.

DETAILED DESCRIPTION OF THE PREFERRED EMBODIMENTS

Throughout this application, the text refers to various embodiments relating to compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the instant invention.

DEFINITIONS

As used herein, certain terms may have the following defined meanings. As used in the specification and claims, the singular form "a," "an" and "the" include singular and plural references unless the context clearly dictates otherwise.

The term "comprising" is intended to mean that the compounds and methods include the recited elements, but not excluding others. "Consisting essentially of" when used to define compositions and methods, shall mean excluding other elements of any essential significance to the compounds or methods. "Consisting of" shall mean excluding more than trace elements of other ingredients for claimed compounds and substantial method steps. Embodiments defined by each of these transitional terms are within the scope of this invention. Accordingly, it is intended that the processes and compositions can include additional steps and components (comprising) or alternatively include additional steps and compounds of no significance (consisting essentially of) or alternatively, intending only the stated methods steps or compounds (consisting of).

Neutral pH or approximately neutral pH refers to a ph of about $7.0\pm0.5$.

The term "acidic" as used herein refers to an acidic pH range generally produced from by-products of bacterial growth. Such acidic pHs generally range from above 1 to about 6.5 and, preferably, a pH range of from 2 to about 5. A strong acid has a pH of below 2.0.

The term "indicator" refers to a substance capable of changing color with a change in pH caused when a threshold amount of bacterial by-products are produced. In one embodiment, the indicator is a pH indicator. Such pH indicators are sometimes referred to herein as "pH indicating moieties."

The term "bodily fluids" refers to fluids that are derived from the body, fluids that are intended to be administered into the body, and fluids that contact the body. The term "eye fluids" refers to fluids present in the eye, administered to the eye, and/or fluids that contact the eye.

The term "eye enzymes" refers to one or more naturally occurring enzymes found in the eye (especially human eyes) and which are preferably not found in cleaning solutions used when the contact lens is removed from the eye. Eye enzymes and substrates are well known in the art. By way of example, eye enzymes and their substrate include lysozyme/peptidoglycans, transketolase/phosphorylated and non-phosphorylated monosaccharides, and transglutaminases/glutamine residues.

Methods and Lenses

In one aspect, this invention provides a contact lens comprising pH indicating moieties useful for determining the presence or absence of active bacterial infections wherein said pH indicator is entrapped in the lens. The pH indicating moieties in the lens are employed in an amount effective for detecting a color change thereby evidencing a change in pH. As used herein, the term "detection" denotes a color-change visible by human eye having ordinary vision.

The pH indicator moieties allow for the visual detection of bacterial growth. In certain embodiments the pH indicating moieties are selected from heptamethoxy red and hexamethoxy red or a combination thereof. In another embodiment, the pH indicating moieties are a derivative of heptamethoxy red or hexamethoxy red. Other examples of pH indicator moieties useful in the invention include bromocresol purple (5',5"-dibromo-o-cresolsulfonephthalein), bromocresol green (tetrabromo-m-cresolsulfonephthalein), o-cresol red (o-cresolsulfonephthalein), phenol red, bromothymol blue (3',3"-dibromothymolsulfonephthalein), neutral red (3-amino-7-dimethylamino-2-methylphenazine chloride), pentamethoxy red, hexamethoxy red and heptamethoxy red, and combinations thereof.

In one embodiment, the pH indicator is one that exhibits a first color at the pH of normal eye fluids and a second color when the pH changes due to bacterial byproducts and/or bacterial growth. The pH of normal eye fluids is typically about 7.4. pH indicators useful in this invention are typically those that exhibit one color at a pH of about 7.4 and another color at an acidic pH. An acidic pH is less than 6.5. In certain embodiments the color change occurs at a pH of less than about 6.5 or less than about 6.0 or less than about 5.5. This is consistent with the use of most soft lens cleaning solutions which have a pH of 6.6 or higher. See, for example, http://journals.lww.com/optvissci/Fulltext/2008/02000/Physical_Properties_of_Soft_Contact_Lens_Solutions.11.aspx.

In a preferred embodiment, the pH indicator is optically transparent at a pH of normal eye fluids. In a related embodiment, the pH indicator is optically transparent at a pH of about 6.5 to about 8, or about 6.5 to about 7.5, or about 7.0 to about 7.8, or about 6.8 to about 7.8. In a related embodiment, the pH indicator is one that becomes colored at a pH of less than about 6.5, or less than about 6.3, or less than about 6.1, or less than about 6.0, or less than about 5.8, or less than about 5.6, or less than about 5.4, or less than about 5.2, or less than about 5.0, or less than about 4.8.

In one aspect the pH indicator is one that detects pH change associated with by-products of bacterial growth. Bacterial by-products include, but are not limited to, gaseous carbon dioxide, hydrogen sulfide, sulfur dioxide, hydrogen, ammonium, lactate, and mixtures thereof. Mixtures of these by-products with moisture result in the formation of acids such as carbonic acid, sulfuric acid, ammonium hydroxide, lactic acid, or mixtures thereof.

The pH indicators useful in this invention are those that detect bacterial growth from active bacterial infections due to contaminating microorganisms. Examples of contaminating microorganisms include *Staphylococcus aureus, Salmonella, Staphylococcus epidermidis, Streptococcus mitis, Streptococcus sanguis, Enterococcus faecium, Escherichia coli, Enterobacter cloacae, Enterobacter aerogenes, Enterococcus faecalis, Pseudomonas aeruginosa, Klebsiella pneumonia, Candida albicans, Bacillus, Brucella, Campylobacter, Clostridium, Escherichia coli, Listeria monocytogenes, Salmonella, Streptococcus, Pseudomonas aeruginosa, Staphylococcus aureus, Shigella, Vibrio, Yersinia, Chlamydia trachomatis, Neisseria gonorrhoeae, Corynebacterium diphtheriae, Acanthamoeba*, gram negative bacilli, bacteria of the genus *Moraxella*, or a combination thereof.

The pH indicators of this invention can be incorporated into the lens in such a way that does not obscure the vision of the user. In one embodiment, the pH indicating moieties are entrapped within the portion of the lens that is not covering the pupil of the eye. FIG. 1 depicts a diagram of the eye and the portion that is referred to as the pupil. As can be appreciated by the skilled artisan, it is contemplated that the pH indicating moieties can be placed in a variety of places on the lens without obscuring the vision of the user. In one embodiment, the pH indicating moieties are placed on the lens in a design such as a circle with a line through it, a thick diagonal marking, or any other design that will quickly be recognized by the wearer to mean that the lens is no longer suitable for use. In another embodiment, the design can include a motif or variegated type pattern such as hatch marks or a sub-field of lattice-like x's appearing in the margins of the lens. Such placement of the pH indicating moieties can be accomplished in a variety of ways. For example, the pH indicating moieties can be printed on the lens and then an additional hydrogel layer can be applied over the pH indicating moieties to entrap them in the lens to prevent leaching. pH indicating moieties may also be printed or stamped on a contact mold. The mold would then be filled with the lens hydrogel to entrap the pH indicating moieties in the lens. In one embodiment, the contact lens is mildly cross-linked so to further entrap the pH indicator therein. US patent publication 2011/0230588 describes methods of making hydrogel or soft contact lenses and US patent publication 2008/0012164 describes methods of printing substances onto such contact lenses. Each of these references is herein incorporated by reference.

The pH indicators are also impervious to long term soaking, cleaning, or storage so that the pH indicating properties are maintained in solutions typically used for cleaning and storing contact lenses. Such cleaning and storage solutions are commonly known in the art and include, for example, saline solution, buffering solutions and enzymatic cleaners used in protein removal, and solutions containing hydrogen peroxide.

Another aspect of this invention relates to a contact lens comprising one or more indicators entrapped in the lens wherein the indicator is a lifespan indicator and further wherein the lens comprises particles comprising a biodegradable outer layer and a biocompatible colorant in the interior of the particle. Biodegradation of the exterior of the particles is predicated by use of an eye enzyme in the exterior of the particles and degradation time is selected such that release of the colorant indicates that the lens is no longer suitable for use. The colorant, like the pH indicating moieties should be applied over a portion of the lens in a manner that does not obscure the vision of the user. In one embodiment, the colorant and biodegradable layer is applied over the portion of the lens that does not cover the pupil of the eye.

In one embodiment, the colorant is biocompatible. Examples of biocompatible colorants can be found in US patent publication 2008/0012164 which is herein incorporated by reference. Preferably, the exterior of the colorant particle is white and the particles are placed at or near the edge of the lens such that it is overlays the sclera so as to be less noticeable. The interior of the colorant particles comprise a food dye, pH indicators, and the like such that upon biodegradation of the exterior of the particle, release of the interior components will result in a color change in that portion of the lens. In a preferred embodiment, the colorant particle is placed on or at surface of the lens by printing the particle onto the surface of the mold half optionally in the presence of a thixotropic agent to retain the printed particle at the desired location. Subsequently, the monomer mix used to form the lens is added. Upon closure of the mold and polymerization, the particle is entrapped in the lens to provide a smooth lens surface such as not to cause discomfort to the wearer. See, for example, U.S. Pat. No. 5,158,718 which is incorporated herein by reference in its entirety.

In one embodiment, the biodegradable or the outer layer corresponds to the usable lifespan of the lens. In another embodiment, the biodegradable outer layer is translucent and the colorant particle is optically visible to the user. As the layer degrades, the lens will lose this colorant. When the colorant can no longer be detected by the user, it is an indication of the expiration of the contact lens. In a related embodiment, the colorant is a pH indicator the exhibits one color at the pH of normal eye fluids and another color at a pH of below 6.5. Thus, the pH indicator acts as both an indicator of lifespan and an indicator of active bacterial infections. A change in the color would indicate an active bacterial infection and a loss of color would indicate that the lens is not within the usable lifespan.

In another embodiment, the lens comprises a life-span indicator comprising colorant particles with a biodegradable outer layer and a biocompatible colorant in the interior of the particle and a pH indicator for the detection of the presence or absence of active bacterial infections. The lifespan indicator and the pH indicator can be positioned at different parts of the lens.

In another embodiment, the colorant particle has an interior comprising a colorant entrapped in it and an outer layer comprised of a biodegradable layer wherein the biodegradation of the outer layer corresponds to the usable lifespan of the lens. The biodegradable material used on the surface of the printed particle is one which reacts with one or more enzymes naturally found in the eye fluid. This permits the lens to be maintained and stored in aqueous solutions without degradation of the printed particle. Like the pH indicating moieties, the colorant particles should be also impervious to cleaning and storing solutions. In contrast, the longer the lens is on the eye, the more the surface of the printed particle degrades. The thickness of the surface is, of course, dependent on the rate of biodegradation which can be readily determined by the skilled artisan. Once the surface has eroded, the interior is then contacted with eye fluid which will initiate a color or color change. In a related embodiment, the surface of the printed particle also contains a material that colors the particle white. One example is titanium dioxide. The white particle on the sclera of the eye causes the particle to "blend" in when the outer coating is in tact. Continued wear in the eye can cause the white outer layer of the particle to degrade, leaving the colorant exposed. In one embodiment, the printed particle is placed on the lens in a design such as a circle with a line through it or any other design that will quickly be recognized by the wearer to mean that the lens is no longer suitable for use. In another embodiment, the design can include a motif or variegated type pattern such as hatch marks or a sub-field of lattice-like x's appearing in the margins of the lens. Indeed, if the color and the design is such, third parties will be able to advise the wearer that the lens is no longer suitable for use. In a related embodiment, the colorant in the interior of the layer is mixed with a thixotropic agent to prevent leeching or migration of the colorant particle within or out of the lens.

In some instances, it may be necessary or desirable to micronize the colorant particles before casting them into the contact lens. Techniques to micronize solutions or suspensions are well known in the art. Traditional micronization techniques are based on friction to reduce particle size. Such methods include milling, bashing and grinding. A typical industrial mill is composed of a cylindrical metallic drum that usually contains steel spheres. As the drum rotates the spheres inside collide with the particles of the solid, thus crushing them towards smaller diameters. In the case of grinding, the solid particles are formed when the grinding units of the device rub against each other while particles of the solid are trapped in between.

Methods like crushing and cutting are also used for reducing particle diameter, but produce more rough particles compared to the two previous techniques (and are therefore the early stages of the micronization process). Crushing employs hammer-like tools to break the solid into smaller particles by means of impact. Cutting uses sharp blades to cut the rough solid pieces into smaller ones.

Modern methods use supercritical fluids in the micronization process. The most widely applied techniques of this category include the RESS process (Rapid Expansion of Supercritical Solutions), the SAS method (Supercritical Anti-Solvent) and the PGSS method (Particles from Gas Saturated Solutions).

In the case of RESS, the supercritical fluid is used to dissolve the solid material under high pressure and temperature, thus forming a homogeneous supercritical phase. Thereafter, the solution is expanded through a nozzle and small particles are formed. At the rapid expansion point right at the opening of the nozzle there is a sudden pressure drop that forces the dissolved material (the solid) to precipitate out of the solution. The crystals that are instantly formed enclose a small amount of the solvent that, due to the expansion, changes from supercritical fluid to its normal state (usually gas), thus breaking the crystal from inside-out. At the same time, further reduction of size is achieved while the forming and breaking crystals collide with each other at the vicinity of the nozzle. The particles that are formed this way have a diameter of a few hundreds of nanometers.

In the SAS method, the solid material is dissolved in an organic solvent and a supercritical fluid is then also forced by means of pressure to dissolve in the system. In this way, the volume of the system is expanded, thus lowering the density, and therefore also the solubility of the material of interest is decreased. As a result, the material precipitates out of the solution as a solid with a very small particle diameter.

In the PGSS method the solid material is melted and the supercritical fluid is dissolved in it, like in the case of the SAS method. However, in this case the solution is forced to expand through a nozzle, and in this way nanoparticles are formed.

In all three methods described, the effect that causes the small diameter of the solid particles is the supersaturation that occurs at the time of the particle formation, like it was described in more detail in the case of the RESS process. The PGSS method has the advantage that because of the supercritical fluid, the melting point of the solid material is reduced. Therefore, the solid melts at a lower temperature than the normal melting temperature at ambient pressure. In addition, all these new techniques do not demand long processing times, like in the case of the traditional methods. As a result, they are thought to be more appropriate when thermolabile materials need to be processed (like pharmaceuticals and foodstuff ingredients).

Another aspect of this invention relates to a contact lens comprising pH indicating moieties useful for determining the presence or absence of active bacterial infections. In one embodiment, the lens also contain particles entrapped within the lens as described above which are used as an indicator of the usable life-span of the lens. That is to say that the lens contains a first colorant trapped in the particles for assessing usable life-span of the lens and a second colorant that is a pH indicator that changes when there is an active bacterial infection occurring in or on the eye. In one embodiment, the colorant and/or colorant particles are water insoluble such that they will not migrate throughout the biodegradable layer or hydrogel to cover the pupil portion of the eye.

Table 1 depicts examples of pH indicators suitable for use as the colorant particle.

TABLE 1

| Indicator | Low pH color | Transition pH range | High pH color |
| --- | --- | --- | --- |
| Gentian violet (Methyl violet 10B) | Yellow | 0.0-2.0 | blue-violet |
| Leucomalachite green (first transition) | Yellow | 0.0-2.0 | Green |
| Leucomalachite green (second transition) | Green | 11.6-14 | Colorless |
| Thymol blue (first transition) | Red | 1.2-2.8 | Yellow |
| Thymol blue (second transition) | Yellow | 8.0-9.6 | Blue |
| Methyl yellow | Red | 2.9-4.0 | Yellow |
| Bromophenol blue | Yellow | 3.0-4.6 | Purple |
| Congo red | blue-violet | 3.0-5.0 | Red |
| Methyl orange | Red | 3.1-4.4 | Orange |
| Bromocresol green | Yellow | 3.8-5.4 | Blue |
| Methyl red | Red | 4.4-6.2 | Yellow |
| Methyl red | Red | 4.5-5.2 | Green |
| Azolitmin | Red | 4.5-8.3 | Blue |
| Bromocresol purple | Yellow | 5.2-6.8 | Purple |
| Bromothymol blue | Yellow | 6.0-7.6 | Blue |
| Phenol red | Yellow | 6.4-8.0 | Red |
| Neutral red | Red | 6.8-8.0 | Yellow |
| Naphtholphthalein | colorless to reddish | 7.3-8.7 | greenish to blue |
| Cresol Red | Yellow | 7.2-8.8 | reddish-purple |
| Alizarine Yellow R | Yellow | 10.2-12.0 | Red |

Biodegradable coatings are well known in the art. Preferably, the biodegradable coating is hydrophilic to allow for proper wetting of the contact lens. Hydrophilic lenses decrease the adherence of the lens to the eye and reduce the proteinaceous deposits on the lens. Some examples of biodegradable coatings include, but are not limited to, PGLA, PLLA, PGA, PDLLA, PCL, PDLGA, PLDLA, PLC (all of which are available from Zeus, 3737 Industrial Blvd, Orangeburg, S.C., 29118 USA under the tradename Absorv™), hylaurinic acid, alginate, polyhydroxyalkanoates, dextran; poly(ethylene glycol); poly(ethylene oxide); mannitol; poly (hydroxalkanoate)s of the PHB-PHV class; and other modified poly(saccharides) such as starch, cellulose and chitosan, and the like. Other biodegradable polymers include collagen, gelatin, albumin, casein, fibroin, fibrin, laminin, fibronectin, and vitronectin. Also useful are the bioresorbable polymers described in US patent publication 2010/0317745 which is herein incorporated by reference.

In one of its method aspects, there is a provided a method for assessing whether a reusable contact lens is in contact with an eye surface having an active bacterial infection which method comprises detecting the presence or absence of a colorimetric change in the pH indicating moieties entrapped within one of the lenses according to this invention; correlating the presence or absence of a colorimetric change in the pH indicator with the presence of an active bacterial infection on the eye; and wherein a colorimetric change correlates to the presence of an active bacterial infection and the lack of a colorimetric change correlates to the absence of an active bacterial infection.

The above aspect of this invention is predicated on the fact that hydrogels have a high water content and will allow diffusion of protons from the eye fluid into the lens. These protons are generated by carbon dioxide and other bacterial by-products when they contact water. Carbon dioxide, for example, will generate carbonic acid when it is contacted with water.

In one embodiment, the method also comprises assessing whether a reusable contact lens of limited lifespan is within the usable lifespan of the lens wherein the method comprises detecting the presence or absence of a biocompatible colorant useful for determining the usable lifespan of the lens; correlating the presence or absence of a colorant with the usable lifespan of the lens.

EXAMPLES

In the examples below as well as throughout the application, the following abbreviations have the following meanings. If not defined, the terms have their generally accepted meanings ° C.=degrees Celsius
DE=Diatomaceous earth
° F.=Degrees Fahrenheit
g=Gram
IPA=Isopropyl Alcohol
kg=Kilogram
L=Liter
M=Molar
° C.=Degrees Celsius
mbar=Millibar
mg=Milligram
min=Minutes
mL=Milliliter
MW=Molecular Weight
m/z=Mass/Charge
PE=Polyethylene
PVOH=Polyvinyl Alcohol
RT=Room Temperature
w/w=Weight to weight Example 1

Preparation of Heptamethoxy Red in Gram Scale

Step 1: Synthesis of Methyl 2,4,6-trimethoxybenzoate (CAS #29723-28-2)

2,4,6-trimethoxybenzoic acid (CAS #570-02-5) (5.61 g, 26.42 mmol) was suspended in 20 mL of methanol (CAS

67-56-1). Concentrated sulfuric acid (CAS #7664-93-9) (1 mL) was added to the mixture, and the reaction heated to reflux for 24 hrs. The reaction was cooled to room temperature, and the methanol (CAS #67-56-1) removed in vacuo. The residues were taken up in 50 mL 5% NaHCO$_3$ (CAS #144-55-8) and extracted with hexane (CAS #110-54-3) until all the solids had dissolved. The hexane extract was dried over anhydrous Na$_2$SO$_4$ (CAS #7757-82-6), filtered, and rotovapped to dryness to give the desired product, methyl 2,4,6-trimethoxybenzoate (CAS #29723-28-2), as a white crystalline solid.

Step 2: Synthesis of Heptamethoxy Red 1-bromo-2,4-dimethoxybenzene (CAS #17715-69-4) (4.23 g, 19.47 mmol) was added to a round bottom flask, and the flask flushed with nitrogen for 10 minutes. Anhydrous ether (CAS #60-29-7) (80 mL) was added, followed by the drop wise addition of n-butyllithium (CAS #109-72-8) in hexane (CAS #110-54-3) (1.6 M, 12.2 mL). The cloudy mixture was stirred at room temperature for 10 minutes. Methyl 2,4,6-trimethoxybenzoate (CAS #29723-28-2) (2.20 g, 9.74 mmol) was dissolved in ether (CAS #60-29-7), and added drop wise to the reaction mixture. After the addition was complete, the reaction was stirred for 3 minutes longer. The reaction was then poured into a separatory funnel containing 5% NH$_4$Cl (CAS #12125-02-9) (50 mL) and shaken until a color change was observed. The layers were separated, and the ether layer was dried over anhydrous Na$_2$SO$_4$ (CAS #7757-82-6), filtered, and rotovapped to dryness. The crude oil was placed in the freezer (6.02 g, 132% due to impurities).

Example 2

One Step Preparation of Heptamethoxy Red

Add (4.23 g, 19.47 mmol) 1-bromo-2,4-dimethoxybenzene (CAS #17715-69-4) to an appropriately sized round bottom flask. Attach a rubber septum to seal the flask.

Insert a needle into the septum as a vent and flush the round bottom flask with nitrogen for about 10 minutes.

Add (80 mL) anhydrous ether (CAS #60-29-7), followed by the drop wise addition of n-butyllithium (CAS #109-72-8) in hexane (CAS #110-54-3) (1.6 M, 12.2 mL).

Stir the cloudy mixture for 10 minutes and keep the round bottom flask on ice.

Dissolve (2.20 g, 9.74 mmol) of methyl 2,4,6-trimethoxybenzoate (CAS #29723-28-2) in about 20 ml of anhydrous ether (CAS #60-29-7) (more than ~20 mL can be used if needed), and then add this drop wise to the reaction mixture.

After the addition is complete, stir the reaction mixture for about 3 minutes longer.

Pour the reaction mixture into a separatory funnel containing 5% NH$_4$Cl (aq) (CAS #12125-02-9) (50 mL) and shake until a color change is observed (pale orange).

The layers are allowed to separate, and dry the top ether layer with about 5 g anhydrous Na$_2$SO$_4$ (CAS #7757-82-6), filter, and rotovapped to dryness at 35-40° C. under 400 mbar.

Place the crude oil of heptamethoxy red (yellow-orange in color) into the freezer.

Yield is ~3.1 g.

Example 3

Preparation of Hexamethoxy Red in Gram Scale

Add (4.23 g, 19.47 mmol) 1-bromo-2,4-dimethoxybenzene (CAS #17715-69-4) to an appropriately sized round bottom flask.

Attach a rubber septum to seal the flask.

Insert a needle into the septum as a vent and flush the round bottom flask with nitrogen for about 10 minutes.

Add (80 mL) anhydrous ether (CAS #60-29-7), followed by the drop wise addition of n-butyllithium (CAS #109-72-8) in hexane (CAS #110-54-3) (1.6 M, 12.2 mL).

Stir the cloudy mixture for 10 minutes and keep the round bottom flask on ice.

Dissolve (2.20 g, 9.74 mmol) of methyl 2,4-dimethoxybenzoate (CAS #2150-41-6) in about 20 ml of anhydrous ether (CAS #60-29-7) (more than about 20 ml can be used if needed), and then add this drop wise to the reaction mixture.

After the addition is complete, stir the reaction mixture for about 3 minutes longer.

Pour the reaction mixture into a separatory funnel containing 5% NH$_4$Cl (aq) (CAS #12125-02-9) (50 mL) and shake until a color change is observed (pale orange).

The layers are allowed to separated, and dry the top ether layer with about 5 g anhydrous Na$_2$SO$_4$ (CAS #7757-82-6), filter, and rotovapped to dryness at 35-40° C. under 400 mbar.

Place the crude oil of hexamethoxy red (yellow-orange in color) into the freezer.

Yield is about 3.1 g.

Example 4

Preparation of Contact Lenses with Indicators

Contact lenses with indicators can be prepared according to the following disclosure. The colorant and/or pH indicator can optionally be mixed with a thixotropic agent and/or optionally with oligomers of HEMA. "HEMA" refers to hydroxyethylmethacrylate and has the following monomeric structure:

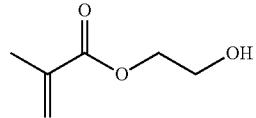

The colorant and/or pH indicator mixture can then be micronized, if necessary, and optionally, a coating of titanium oxide and enzyme substrate can be provided to allow for a degradable white surface. The particles can then be positioned or stamped onto the mould surface at the position corresponding to the desired placement of the colorant and/or pH indicator. In another embodiment, the mould can be subjected to corona discharge of 28 KV at 22 Hz for 1 second in the position corresponding to the area in which the colorant and/or pH indicator is desired. The colorant and/or pH indicator particles can then be applied to the treated area.

The mould can then be completed and injected with a lens monomer mix. A lens monomer mix can be prepared, for example, from 99.3 weight percent hydroxyethyl methacrylate, 0.5 weight percent ethyleneglycol dimethyacrylate and 0.2 weight percent benzoin methyl ether. Polymerization can be carried out by ultraviolet light irradiation. The lens can then finished through the routine processing steps and hydrated and packaged.

What is claimed is:

1. A contact lens comprising one or more indicators entrapped in the lens wherein the indicator is a pH indicator useful for determining the presence or absence of an active bacterial infections in the eye by contacting the pH indicator with an eye fluid and wherein the pH indicating moieties are optically transparent at a pH of about 6.8 to about 7.6 and become colored at a pH of less than about 6.5.

2. The lens of claim 1, wherein the pH indicating moieties detect pH change associated with by-products of bacterial growth selected from the group consisting of gaseous carbon dioxide, hydrogen sulfide, sulfur dioxide, hydrogen, ammonium, lactate, and mixtures thereof.

3. The lens of claim 1, wherein the pH indicator is selected from heptamethoxy red and hexamethoxy red.

4. The lens of claim 1, wherein the lens comprises a lifespan indicator comprising a biodegradable outer layer and a colorant particle in the interior of the particle, wherein the biodegradation of the outer layer corresponds to the usable lifespan of the lens.

5. A method for assessing whether the eye of the wearer of a reusable contact lens of limited life has an active bacterial infection detectable in the eye fluid of the wearer which method comprises
   detecting the presence or absence of a colorimetric change in the pH indicating moieties entrapped within the lens according to claim 1;
   correlating the presence or absence of a colorimetric change in the pH indicator with the presence of an active bacterial infection on the lens; and
   wherein a colorimetric change correlates to the presence of an active bacterial infection and the lack of a colorimetric change correlates to the absence of an active bacterial infection.

6. The method of claim 5, further comprising assessing whether a reusable contact lens of limited lifespan is within the usable lifespan of the lens wherein the method comprises
   assessing the visibility of a biocompatible colorant useful for determining the usable lifespan of the lens;
   correlating the visibility of a colorant with the usable lifespan of the lens; and
   wherein a visible colorant correlates to an expired lens and the lack of a visible colorant correlates to a lens that is within the usable lifespan.

7. The method of claim 6, wherein the pH indicating moieties are optically transparent at a pH of about 6.8 to about 7.6.

8. The method of claim 6, wherein the pH indicating moieties become colored at a pH of less than about 6.5.

9. The method of claim 6, wherein the pH indicating moieties detect pH change associated with by-products of bacterial growth selected from the group consisting of gaseous carbon dioxide, hydrogen sulfide, sulfur dioxide, hydrogen, ammonium, lactate, and mixtures thereof.

10. The method of claim 6, wherein the pH indicators detect active bacterial infection as a result of contaminating microorganism selected from the group consisting of *Staphylococcus aureus, Salmonella, Staphylococcus epidermidis, Streptococcus mitis, Streptococcus sanguis, Enterococcus faecium, Escherichia coli, Enterobacter cloacae, Enterobacter aerogenes, Enterococcus faecalis, Pseudomonas aeruginosa, Klebsiella pneumonia, Candida albicans, Bacillus, Brucella, Campylobacter, Clostridium, Escherichia coli, Listeria monocytogenes, Salmonella, Streptococcus, Pseudomonas aeruginosa, Staphylococcus aureus, Shigella, Vibrio, Yersinia, Chlamydia trachomatis, Corynebacterium diphtheriae*, gram negative bacilli, bacteria of the genus *Moraxella*, or a combination thereof.

11. The method of claim 6, wherein the pH indicator is selected from heptamethoxy red and hexamethoxy red.

* * * * *